US012721600B2

(12) United States Patent
Ben-Ezra

(10) Patent No.: US 12,721,600 B2
(45) Date of Patent: Sep. 1, 2026

(54) ACOUSTIC FIELD MAPPING WITH ULTRASONIC PARTICLE VELOCITY ESTIMATOR

(71) Applicant: NINA MEDICAL LTD, Nazereth (IL)

(72) Inventor: Shmuel Ben-Ezra, Pardes-Hanna (IL)

(73) Assignee: NINA MEDICAL LTD, Nazereth (IL)

( * ) Notice: Subject to any disclaimer, the term of this patent is extended or adjusted under 35 U.S.C. 154(b) by 149 days.

(21) Appl. No.: 16/964,057

(22) PCT Filed: Jan. 22, 2019

(86) PCT No.: PCT/IL2019/050089
§ 371 (c)(1),
(2) Date: Jul. 22, 2020

(87) PCT Pub. No.: WO2019/145945
PCT Pub. Date: Aug. 1, 2019

(65) Prior Publication Data

US 2021/0045714 A1 Feb. 18, 2021

Related U.S. Application Data

(60) Provisional application No. 62/621,140, filed on Jan. 24, 2018.

(51) Int. Cl.
*A61B 8/00* (2006.01)
*A61B 34/30* (2016.01)
*A61N 7/00* (2006.01)

(52) U.S. Cl.
CPC .......... *A61B 8/4488* (2013.01); *A61B 8/4477* (2013.01); *A61B 8/488* (2013.01);
(Continued)

(58) Field of Classification Search
CPC ....... A61B 8/4488; A61B 8/4477; A61B 8/52; A61B 8/5223; A61N 7/00; A61N 2007/0056
See application file for complete search history.

(56) References Cited

U.S. PATENT DOCUMENTS 5,086,775 A 2/1992 Parker et al.
5,109,857 A 5/1992 Roundhill et al.
(Continued)

FOREIGN PATENT DOCUMENTS

KR 20130034987 4/2013
KR 20170091813 A 8/2017
(Continued)

OTHER PUBLICATIONS

Vaezy et al. ("Real-Time Visualization of High-Intensity Focused Ultrasound Treatment Using Ultrasound Imaging"), 2001, Ultrasound in Med. & Biol., vol. 27, No. 1, pp. 33-43 (Year: 2001).*
(Continued)

*Primary Examiner* — Andrew W Begeman
(74) *Attorney, Agent, or Firm* — The Roy Gross Law Firm, LLC; Roy D. Gross

(57) ABSTRACT

A first transducer (20) transmits a first acoustic field (22) at a first frequency into a region (24) of a medium (26), generating oscillatory motion of scatterers (28) disposed in the region. A second transducer (30) transmits acoustic pulses (32, 34) into the region, and receives respective echoes of each pulse scattering off an oscillating scatterer in the region. The pulses are synchronized with the first acoustic field such that a first pulse scatters off the oscillating scatterer when the scatterer is at a first displacement extremum (36), and a second pulse scatters off the oscillating scatterer when the scatterer is at a second displacement extremum (38) that is opposite the first displacement extremum. A computer processor (29) extracts a time shift between the received echoes, calculates a displacement amplitude of the scatterer, and outputs an indication of the displacement amplitude of the scatterer. Other applications are also described.

20 Claims, 5 Drawing Sheets

(52) U.S. Cl.
CPC .............. *A61B 8/52* (2013.01); *A61B 8/5223* (2013.01); *A61B 34/30* (2016.02); *A61N 7/00* (2013.01); *A61B 8/4405* (2013.01); *A61N 2007/0056* (2013.01)

(56) References Cited

U.S. PATENT DOCUMENTS

| | | | |
|---|---|---|---|
| 5,224,482 A | 7/1993 | Nikoonahad et al. | |
| 5,425,370 A * | 6/1995 | Vilkomerson | A61B 8/0841 600/463 |
| 5,472,405 A | 12/1995 | Buchholtz et al. | |
| 5,919,139 A | 7/1999 | Lin | |
| 6,086,535 A | 7/2000 | Ishibashi et al. | |
| 6,128,523 A | 10/2000 | Bechtold et al. | |
| 6,425,867 B1 | 7/2002 | Vaezy et al. | |
| 6,454,713 B1 | 9/2002 | Ishibashi et al. | |
| 6,485,423 B2 | 11/2002 | Angelsen et al. | |
| 6,786,097 B2 | 9/2004 | Song et al. | |
| 6,875,176 B2 | 4/2005 | Mourad et al. | |
| 7,876,149 B2 | 1/2011 | Song et al. | |
| 8,337,434 B2 | 12/2012 | Vaezy et al. | |
| 8,743,657 B1 | 6/2014 | Barton, III et al. | |
| 9,107,798 B2 | 8/2015 | Azhari et al. | |
| 9,420,988 B2 | 8/2016 | Anand et al. | |
| 9,743,909 B1 * | 8/2017 | Sapozhnikov | A61B 5/0062 |
| 10,154,826 B2 | 12/2018 | Singh et al. | |
| 10,281,568 B2 | 5/2019 | Oelze et al. | |
| 2003/0115963 A1 | 6/2003 | Song et al. | |
| 2003/0204141 A1 | 10/2003 | Nock et al. | |
| 2004/0003430 A1 | 1/2004 | Hauptmann et al. | |
| 2004/0034304 A1 * | 2/2004 | Sumi | G01S 7/52042 600/439 |
| 2004/0034305 A1 | 2/2004 | Song et al. | |
| 2004/0267129 A1 | 12/2004 | Angelsen et al. | |
| 2005/0203399 A1 | 9/2005 | Vaezy et al. | |
| 2007/0106157 A1 * | 5/2007 | Kaczkowski | A61B 8/587 600/438 |
| 2007/0167774 A1 | 7/2007 | Jeong et al. | |
| 2007/0232912 A1 | 10/2007 | Chen et al. | |
| 2007/0239077 A1 | 10/2007 | Azhari et al. | |
| 2007/0276245 A1 | 11/2007 | Konofagou | |
| 2008/0058682 A1 | 3/2008 | Azhari et al. | |
| 2008/0097207 A1 * | 4/2008 | Cai | G01S 15/899 601/3 |
| 2008/0312561 A1 | 12/2008 | Chauhan | |
| 2009/0124203 A1 | 5/2009 | Song et al. | |
| 2009/0209858 A1 | 8/2009 | Oelze | |
| 2010/0160781 A1 | 6/2010 | Carter et al. | |
| 2010/0274130 A1 | 10/2010 | Anand et al. | |
| 2010/0274161 A1 | 10/2010 | Azhari et al. | |
| 2010/0280373 A1 | 11/2010 | Fan et al. | |
| 2010/0286514 A1 | 11/2010 | Leighton et al. | |
| 2011/0184322 A1 | 7/2011 | Brawer et al. | |
| 2011/0251524 A1 | 10/2011 | Azhari et al. | |
| 2013/0184580 A1 * | 7/2013 | Lause | G01S 7/52074 600/440 |
| 2014/0147013 A1 | 5/2014 | Shandas et al. | |
| 2014/0150556 A1 | 6/2014 | Angelsen et al. | |
| 2015/0164480 A1 * | 6/2015 | Watanabe | A61B 8/5246 600/440 |
| 2016/0012114 A1 | 1/2016 | Osborne et al. | |
| 2016/0120511 A1 | 5/2016 | Azuma et al. | |
| 2016/0131749 A1 | 5/2016 | Kim | |
| 2016/0262727 A1 | 9/2016 | Dayton et al. | |
| 2017/0008025 A1 | 1/2017 | Vincent | |
| 2017/0036040 A1 | 2/2017 | Bergfjord et al. | |
| 2017/0080259 A1 * | 3/2017 | Lu | A61B 18/0206 |
| 2018/0145770 A1 | 5/2018 | Oelze et al. | |
| 2019/0038253 A1 | 2/2019 | Song et al. | |
| 2019/0175139 A1 | 6/2019 | Singh et al. | |
| 2019/0232090 A1 | 8/2019 | Ben-Ezra | |
| 2019/0290939 A1 | 9/2019 | Watson et al. | |
| 2019/0314646 A1 | 10/2019 | Song et al. | |

FOREIGN PATENT DOCUMENTS

| | | | | |
|---|---|---|---|---|
| WO | 20130047960 A1 | 4/2013 | | |
| WO | WO-2013047960 A1 * | 4/2013 | | A61B 8/085 |
| WO | 2018/015944 A1 | 1/2018 | | |
| WO | 2020/181290 A1 | 9/2020 | | |

OTHER PUBLICATIONS

Jeong et al. ("Adaptive HIFU noise cancellation for simultaneous therapy and imaging using an integrated HIFU/imaging transducer"). 2010. Physics in Medicine and Biology. vol. 55, 1889-1902 (Year: 2010).*

Supplementary European Search Report for European Application No. 19743270, issued Sep. 22, 2021, 5pp.

European Search Report dated Dec. 8, 2020, which issued during the prosecution of Applicant's European App No. 17830598.3.

Real-time visualization of high-intensity focused ultrasound treatment using ultrasound imaging (Vaezy et al., Ultrasound in Med. & Biol., vol. 27, No. 1, 2001).

Hyperecho in ultrasound images of HIFU therapy: involvement of cavitation (Rabkin et al., Ultrasound in Med. & Biol., vol. 31, No. 7, 2005).

Acoustic characterization of high intensity focused ultrasound fields: A combined measurement and modeling approach (Canney et al., The Journal of the Acoustical Society of America, vol. 124, No. 4, pp. 2406-2420, Oct. 2008.

Passive cavitation imaging with ultrasound arrays (Salgaonkar et al., The Journal of the Acoustical Society of America, vol. 126, No. 6, Dec. 2009).

Passive spatial mapping of inertial cavitation during hifu exposure (Gyongy et al., IEEE Transactions On Biomedical Engineering, vol. 57, No. 1, Jan. 2010).

Combined passive detection and ultrafast active imaging of cavitation events induced by short pulses of high-intensity ultrasound (Gateau et al., IEEE Transactions on Ultrasonics, Ferroelectrics, and Frequency Control, vol. 58, No. 3, 2011).

Spatiotemporal Monitoring of High-Intensity Focused Ultrasound Therapy with Passive Acoustic Mapping (Jensen et al., Radiology: vol. 2262: No. 1, Jan. 2012).

In Vivo Application and Localization of Transcranial Focused Ultrasound Using Dual-Mode Ultrasound Arrays (Haritonova et al., IEEE Transactions on Ultrasonics, Ferroelectrics, and Frequency Control, vol. 62, No. 12, pp. 2031-2042, 2015).

Passive acoustic mapping utilizing optimal beamforming in ultrasound therapy monitoring (Coviello et al., The Journal of the Acoustical Society of America, vol. 137, No. 5, May 2015).

Real-time monitoring of HIFU treatment using pulse inversion (Song et al., Physics in Medicine & Biology, vol. 58, No. 15, Jul. 17, 2013).

Quantitative frequency-domain passive cavitation imaging (Haworth et al., IEEE Transactions on Ultrasonics, Ferroelectrics, and Frequency Control, vol. 64, No. 1, Jan. 2017).

In vivo real-time cavitation imaging in moving organs (Arnal et al., Physics in Medicine & Biology, vol. 62, No. 3, Jan. 10, 2017).

Visualization of the intensity field of a focused ultrasound source in situ (Nguyen et al., IEEE Transactions on Medical Imaging, vol. 38, No. 1, pp. 124-133, Jan. 2019) [Per IEEE: this article was publicly available as of Jul. 19, 2018 as per https://ieeexplore.ieee.org/abstract/document/8413139)].

Singular value decomposition of received ultrasound signal to separate tissue, blood flow, and cavitation signals (Ikeda et al., Japanese Journal of Applied Physics, vol. 57, 2018).

2D and 3D real-time passive cavitation imaging of pulsed cavitation ultrasound therapy in moving tissues (Suarez et al., Physics in Medicine & Biology, vol. 63, No. 23, Dec. 6, 2018).

PCT Search Report for International Application No. PCT/IL2019/050089, mailed Jun. 18, 2019, 2 pp.

PCT Written Opinion for International Application No. PCT/IL2019/050089, mailed Jun. 18, 2019, 5 pp.

PCT Preliminary Report on Patentability for International Application No. PCT/IL2019/050089, dated Jan. 22, 2019, 6 pp.

(56) References Cited

OTHER PUBLICATIONS

An Office Action summarized English translation and Search Report dated Apr. 26, 2021, which issued during the prosecution of Chinese Patent Application No. 201780055779.9.
PCT Preliminary Report for International Application No. PCT/IL2019/050089; mailed Jul. 28, 2020; 6 pp.
An Office Action dated Mar. 10, 2021, which issued during the prosecution of U.S. Appl. No. 16/246,522.
Bonnefous, O., and Patrick Pesque. "Time domain formulation of pulse-Doppler ultrasound and blood velocity estimation by cross correlation." Ultrasonic imaging 8.2 (1986): 73-85.
Kasai, Chihiro, et al. "Real-time two-dimensional blood flow imaging using an autocorrelation technique." IEEE Transactions on sonics and ultrasonics 32.3 (1985): 458-464.
Jensen, Jørgen Arendt. "Implementation of ultrasound time-domain cross-correlation blood velocity estimators." IEEE transactions on biomedical engineering 40.5 (1993): 468-474.
Munk, Peter. Estimation of blood velocity vectors using ultrasound. Diss. Department of Information Technology, Technical University of Denmark, 2000.
Pulse Shapes, https://www.ldeo.columbia.edu/users/menke/radar/pulse/index.html, downloaded Jan. 21, 2018.
1 Office Action for United States U.S. Appl. No. 16/246,522, mailed Aug. 23, 2021, 48pp.
PCT International Search Report for International Application No. PCT/IL2021/0513001, mailed Jan. 28, 2022, 2pp.
PCT Written Opinion for International Application No. PCT/IL2021/0513001, mailed Jan. 28, 2022, 7pp.
"Tissue Harmonic Imaging: A Review" [W.R. Hedrick Linda Metzger, Journal of Diagnostic Medical Sonography, vol. 21, issue 3, May 2005].
"Feasibility study of ultrasonic computed tomography-guided high-intensity focused ultrasound" [Haim Azhari, Ultrasound in Medicine and Biology, vol. 38, issue 4, Apr. 2012]—Abstract.
"Temperature dependence of acoustic harmonics generated by non-linear ultrasound beam propagation in ex vivo issue and tissue-mimicking phantoms" [Maraghechi et al., International Journal of Hyperthermia, 31:6, published Jul. 1, 2015].
"Photoacoustics: a historical review" [Manohar et al., Advances in Optics and Photonics, vol. 8, issue 4, published Oct. 20, 2016].
"Objective breast tissue image classification using Quantitative Transmission ultrasound tomography" [Malik et al., Scientific Reports 6, article 38857, published Dec. 9, 2016].
"Quantitative transmission ultrasound tomography:imaging and performance characteristics" [Malik et al., Med. Phys. 15(7), published May 28, 2018].
"Nonlinear acoustics and imaging" [Thomas L. Szabo, in Diagnostic Ultrasound Imaging, 2004, chapter 12.5.1]—Abstract.
"Advanced and emerging surgical technologies and the process of innovation" [Russell K. Woo, Thomas M. Krummel, Pediatric Surgery (Sixth Edition), 2006]—Abstract.
U.S. Appl. No. 62/621,140, filed Jan. 24, 2018.
An International Search Report and a Written Opinion both dated Oct. 17, 2017, which issued during the prosecution of Applicant's PCT/IL2017/050799.
An International Search Report and a Written Opinion both dated Jun. 18, 2019, which issued during the prosecution of Applicant's PCT/IL2019/050089.
"An axial velocity estimator for ultrasound blood flow imaging, based on a full evaluation of the Doppler equation by means of a two-dimensional autocorrelation approach" [Loupas et al., IEEE Transactions on Ultrasonics, Ferroelectrics, and Frequency Control, vol. 42, No. 4, Jul. 1995].
"Low-order complex AR models for mean and maximum frequency estimation in the context of Doppler color flow mapping" [Loupas et al., IEEE Transactions on Ultrasonics, Ferroelectrics, and Frequency Control, vol. 37, No. 6, Nov. 1990].
"Experimental evaluation of velocity and power estimation for ultrasound blood flow imaging, by means of a two- dimensional autocorrelation approach" [Loupas et al, IEEE Transactions on Ultrasonics, Ferroelectrics, and Frequency Control, vol. 42, No. 4, Jul. 1995].
"Acoustic Radiation Force Impulse (ARFI) Imaging: a Review" [Kathy Nightingale, Curr Med Imaging Rev. Nov. 1, 2011; 7(4): 328-339].
"Developments in target micro-Doppler signatures analysis: radar imaging, ultrasound and through-the-wall radar" [Clemente et al, EURASIP Journal on Advances in Signal Processing 2013, 2013:47].
"High intensity focused ultrasound (HIFU) focal spot localization using harmonic motion imaging (HMI)" [Han et al., 2015 Phys. Med. Biol. 60 5911-5924, downloaded Sep. 13, 2016].
"Observations of tissue response to acoustic radiation force: opportunities for imaging" [Nightingale et.al., Ultrason. Imaging vol. 24, Issue 3, 2002].
"Ultrasound elastography: Principles and techniques" [Gennisson et al., Diagnostic and Interventional Imaging (2013) 94, 487-495].
"Clinical use of ultrasound tissue harmonic imaging" [Tranquart et al., Ultrasound in Medicine and Biology, vol. 25, Issue 6, 1999].
"Noninvasive diagnosis of congenital and acquired pediatric heart disease" [Philip J. Spevak, Laureen M. Sena, Critical Heat Disease in Infants and Children (second edition), 2006]—Abstract.
United States Patent and Trademark Office, Advisory Action for U.S. Appl. No. 16/246,522, mailed Jan. 21, 2022, 8pp.
United States Patent and Trademark Office, Non-Final Office Action for U.S. Appl. No. 16/246,522, mailed Jul. 21, 2022, 40pp.
United States Patent and Trademark Office, Final Office Action for U.S. Appl. No. 16/246,522, mailed Nov. 1, 2023, 101pp.
Office Action for Chinese Patent Application No. 201980021795.5, dated Nov. 28, 2023, 9pp.
United States Patent and Trademark Office, Notice of Allowance and Fee(s) Due for U.S. Appl. No. 16/246,522, mailed Mar. 13, 2025, 168pp.
European Patent Office, Communication under Rule 71(3) EPC, Intention to Grant and Text Intended for Grant for European Patent Application No. 17830598.3, dated Feb. 24, 2025, 37pp.
European Patent Office, Communication pursuant to Rule 71(3) EPC—Intention to Grant and Text Intended for grant—for European Patent Application No. 19743270.1, dated Dec. 18, 2024, 38pp.
United States Patent and Trademark Office, Final Office Action for U.S. Appl. No. 16/246,522, mailed Apr. 26, 2023, 62pp.

* cited by examiner

ACOUSTIC FIELD MAPPING WITH ULTRASONIC PARTICLE VELOCITY ESTIMATOR

CROSS-REFERENCE TO RELATED APPLICATIONS

The present application is a US National Phase of PCT/IL2019/050089 to Ben-Ezra, filed Jan. 22, 2019, published as WO 2019/145945 to Ben-Ezra, which claims the priority of U.S. Provisional No. 62/621,140 to Ben-Ezra, filed Jan. 24, 2018, entitled, "Acoustic field mapping with ultrasonic particle velocity estimator," of which the content of both applications is incorporated herein by reference.

FIELD OF THE INVENTION

Applications of the present invention relate to acoustic field characterization, measurement, and mapping. More specifically, applications of the present invention relate to image guided therapy, such as image guided high intensity focused ultrasound (HIFU).

BACKGROUND

High intensity focused ultrasound (HIFU), also known as high intensity therapeutic ultrasound (HITU), is a method for non-invasive treatment of internal organs and tissue, e.g., tumors. Ultrasound energy is often used as well for imaging of internal organs and tissue. An ultrasonic A-line, also known as an RF-line, is acquired by using an ultrasound transducer to send an ultrasonic pulse into a medium or a subject's body and receiving an echo of the pulse reflecting off of inhomogeneities within the medium, e.g., a scatterer, a particle, or a boundary. The echo data is detected by the transducer, digitized, and processed. The length of time it takes the echo to reach the ultrasound transducer is indicative of the distance between the transducer and the inhomogeneity. Multiple A-lines, e.g., 100 A-lines, at equally spaced positions and angles, may be used to create a sonogram.

An ultrasonic A-line may be repeatedly pulsed at a pulse repetition frequency (PRF). For any given A-line, a desired penetration depth will limit the PRF, i.e., will limit the time between successive pulses, as each pulse generally cannot be sent before the echo from the immediately previous pulse has been received. If a target, off of which the A-line pulse is reflecting, is moving then the respective echoes from two successive pulses echoing off the target will be shifted (translated) in time. If the velocity of the target is constant over the time interval between the two pulses, then the velocity of the target will be proportional to the shift in time and may be calculated.

A 1985 IEEE Transactions on Sonics and Ultrasonics article entitled "Real-time two-dimensional blood flow imaging using an autocorrelation technique," by Chihiro Kasai et al., describes a blood flow imaging system that combines a conventional pulsed Doppler device and an autocorrelator. Blood flow within a given cross section of a live organ is described as being displayed in real time, with the direction of blood flow and its variance expressed by means of a difference in color and hue respectively. Experiments were conducted with a mechanical and an electrical scanner using phantoms, and a good agreement with the theory is described as being obtained. Studies on clinical significance for normal and diseased hearts are described as having successful results.

A 1986 Ultrasonic Imaging article entitled "Time domain formulation of pulse-doppler ultrasound and blood velocity estimation by cross-correlation," by O. Bonnefous et al., describes that real-time blood flow imaging has become possible thanks to the development of a velocity estimator based on phase-shift measurements of successive echoes, but that the method suffers from well-known limitations of pulse-Doppler instruments. The article presents a new formulation that describes the pulse-Doppler effect on the successive echoes from a cloud of moving targets as a progressive translation in time due to the displacement of the scatterers between two excitations.

The approach is described in the article as allowing the efficient generation of computer-simulated data in order to accurately evaluate various processing techniques. Furthermore, the approach is described as leading to a novel class of velocity estimators in the time domain which measure the time shifts which are proportional to the local blood velocity. A local cross-correlation function is first calculated from a pair of range-gated echoes, and the time shift is then determined by searching for the time position with the maximum correlation. The time-correlation technique is described as providing accurate velocity profiles with broadband transducers. The article describes that classical velocity limitations of pulse-Doppler are overcome because there is no ambiguity in measuring a time shift instead of a phase shift.

The dissertation of Peter Munk, Ph.D., entitled "Estimation of blood velocity vectors using ultrasound," Technical University of Denmark, 2000, describes additional ultrasound techniques.

A 1993 IEEE Transactions on Biomedical Engineering article, entitled "Implementation of ultrasound time-domain cross-correlation blood velocity estimators," by Jorgen Jensen, describes the implementation of real-time blood velocity estimators using time-domain cross-correlation. An algorithm is presented for doing stationary echo canceling, cross-correlation estimation, and subsequent velocity estimation. Sampled data acquired at rates of approximately 20 MHz are used in the algorithm. The algorithm is analyzed with regard to the high sampling frequency, and a method for performing real-time high-speed data movement and cross-correlation is suggested. Implementation schemes based on using the sign of the data as well as the full precision are proposed. From analysis of the process, the article concludes that the sign data implementation can attain real-time processing. The article describes that real-time processing can be obtained for the full precision data as well, but at the expense of using a number of dedicated signal processing chips. Both implantations suggested are described as being able to handle the estimation of velocities for A-lines acquired from multiple directions.

SUMMARY OF THE INVENTION

Methods are described and apparatus provided for assessing a characteristic, e.g., displacement amplitude, particle-velocity, or intensity, of an acoustic field, in accordance with some applications of the present invention. A first acoustic transducer generates a first acoustic field at a first frequency in a region of a medium, which generates oscillatory motion of scatterers disposed within the medium in the region, each scatterer oscillating around a respective equilibrium position. The oscillatory motion of these particles is known as the particle-velocity of the acoustic field and the oscillations occur at the frequency of the first acoustic field. A second acoustic transducer transmits successive pulses into the region and receives respective echoes of each pulse scattering off an oscillating scatterer in the region. Each acoustic pulse has a center frequency that is higher than the first frequency.

In accordance with some applications of the present invention, two pulses that are synchronized with the first acoustic field are used to obtain a measurement of the displacement amplitude of the oscillating scatterer. The time interval between the transmission of first and second pulses is n+0.5 times the period of the first acoustic field, n being a positive integer that is at least 5 and/or less than or equal to 1000, and the two pulses are synchronized with the first acoustic field such that the first pulse scatters off the oscillating scatterer when the oscillating scatterer is at a first displacement extremum, e.g., a maximum positive displacement, with respect to the equilibrium position, and the second pulse scatters off the oscillating scatterer when the oscillating scatterer is at a second displacement extremum that is opposite the first displacement extremum, e.g., a maximum negative displacement, with respect to the equilibrium position. Due to the motion of the oscillating scatterer and the synchronization with the first acoustic field, the displacement that the scatterer undergoes in the time interval between the two pulses is the displacement amplitude of the scatterer. The respective echoes are received at different respective times, each echo being measured from the time that its respective pulse was transmitted. A computer processor is used to extract the time shift between the received echoes and, based on the extracted time shift, calculate the displacement amplitude of the oscillating scatterer.

Alternatively, in accordance with some applications of the present invention, the acoustic pulses are not synchronized with the first acoustic field, e.g., the acoustic pulses are not equally spaced in time and/or are not transmitted at controlled time intervals. The second transducer may transmit at least 5 acoustic pulses into the region, and receive respective echoes of each pulse scattering off an oscillating scatterer. A computer processor is used to extract a series of time shifts. Each time shift in this case may be between any two of the received echoes. A series of displacements may be estimated based on the extracted time shifts, and statistical analysis may be applied to derive the displacement amplitude of the oscillating scatterer.

In accordance with some applications of the present invention, apparatus is provided for determining the location and size of a focal region of HIFU energy emitted at a first frequency into a region in a medium. Location and size of the focal region can be determined by mapping the displacement amplitude, or velocity amplitude of particles in the acoustic field generated by the HIFU energy using acoustic pulses that are transmitted into the region, each pulse having a center frequency that is higher than the first frequency. Imaging ultrasound may be used for guidance of the focal region during treatment. A first acoustic transducer emits HIFU energy to generate a first acoustic field in the region, generating oscillatory motion of scatterers in the region, and an acoustic probe is used for generating imaging ultrasound. Either the acoustic probe or a second transducer transmits two acoustic pulses that are synchronized with the first acoustic field as described hereinabove, and receives respective echoes of the pulses scattering off an oscillating scatterer in the region. A computer processor is used to (a) generate a real-time sonogram of the medium, (b) extract a time shift between the received echoes, (c) based on the extracted time shift, calculate a displacement amplitude of the first acoustic field in the region, and (d) generate a map of displacement amplitudes on a portion of the sonogram corresponding to the region. The area within the region having the highest displacement amplitude corresponds to the area where the intensity of the HIFU energy is the highest, i.e., the focal region of the HIFU energy.

There is therefore provided, in accordance with some applications of the present invention, a method for assessing a characteristic of an acoustic field in a region of a medium, the method including:

driving a first acoustic transducer to transmit a first acoustic field at a first frequency into the region, the first acoustic field generating oscillatory motion at the first frequency of scatterers disposed in the region, each scatterer oscillating around a respective equilibrium position;

driving a second acoustic transducer to:

(a) transmit first and second acoustic pulses into the region, each pulse having a center frequency that is higher than the first frequency, and the time interval between the pulses being n+0.5 times the period of the first acoustic field, n being a positive integer; and (b) receive respective echoes of each pulse scattering off an oscillating scatterer in the region, the first and second pulses being synchronized with the first acoustic field such that the first pulse scatters off the oscillating scatterer when the oscillating scatterer is at a first displacement extremum with respect to the equilibrium position, and the second pulse scatters off the oscillating scatterer when the oscillating scatterer is at a second displacement extremum that is opposite the first displacement extremum with respect to the equilibrium position; and using at least one computer processor:

(a) extracting a time shift between the received echoes that is due to motion of the oscillating scatterer, (b) based on the extracted time shift, calculating a displacement amplitude of the oscillating scatterer, and (c) driving an output device to output an indication of the displacement amplitude of the oscillating scatterer.

For some applications, driving the second acoustic transducer includes driving the second acoustic transducer to transmit first and second acoustic pulses into the region, each pulse having a center frequency that is 5 to 50 times higher than the first frequency.

For some applications, using at least one computer processor further includes:

deriving at least one parameter of the first acoustic field from the displacement amplitude of the oscillating scatterer; and driving the output device to output an indication of the parameter.

For some applications, deriving the at least one parameter of the first acoustic field includes, based on the displacement amplitude, calculating a velocity amplitude of the oscillating scatterer.

For some applications, deriving the at least one parameter of the first acoustic field includes, based on the velocity amplitude, calculating an intensity of the first acoustic field at a location of the oscillating scatterer.

For some applications, driving the second acoustic transducer includes driving the second acoustic transducer to transmit the first and second acoustic pulses into the region, the time interval between the pulses being n+0.5 times the period of the first acoustic field, n being a positive integer greater than or equal to 5.

For some applications, driving the second acoustic transducer includes driving the second acoustic transducer to transmit the first and second acoustic pulses into the region, the time interval between the pulses being n+0.5 times the period of the first acoustic field, and n being a positive integer less than or equal to 1000.

For some applications, driving the first acoustic transducer to transmit the first acoustic field includes driving the first acoustic transducer to transmit high intensity focused ultrasound (HIFU) energy at the first frequency into the region.

For some applications, driving the first acoustic transducer to transmit the HIFU energy includes driving the first acoustic transducer to transmit the HIFU energy at the first frequency, the first frequency being 0.1-5 MHz.

For some applications:

driving the second transducer includes driving the second transducer to:

(a) transmit a plurality of pairs of first and second acoustic pulses into the region in a plurality of respective directions, each pulse having a center frequency that is higher than the first frequency, and the time interval between respective first and second pulses being n+0.5 times the period of the first acoustic field, n being a positive integer, and (b) receive respective echoes of each pulse scattering off a respective oscillating scatterer in the region, each pair of first and second pulses being synchronized with the first acoustic field such that the first pulses scatter off the respective oscillating scatterers when the oscillating scatterers are at respective first displacement extrema with respect to respective equilibrium positions, and the second pulses scatter off the respective oscillating scatterers when the oscillating scatterers are at respective second displacement extrema that are opposite the respective first displacement extrema with respect to the respective equilibrium positions; and using at least one computer processor includes:

(a) extracting respective time shifts between respective pairs of received echoes that are due to motion of the respective oscillating scatterers, (b) based on the extracted time shifts, calculating respective displacement amplitudes of the respective oscillating scatterers, (c) driving an output device to output respective indications of the respective displacement amplitudes of the respective oscillating scatterers, and (d) generating a two-dimensional image of the respective displacement amplitudes in the region.

For some applications, using at least one computer processor further includes:

based on the displacement amplitudes, calculating respective velocity amplitudes of the respective oscillating scatterers;

driving an output device to output respective indications of the respective velocity amplitudes of the respective oscillating scatterers; and generating a two-dimensional image of the respective velocity amplitudes in the region.

For some applications, using at least one computer processor further includes:

based on the velocity amplitudes, calculating respective intensities of the first acoustic field;

driving an output device to output respective indications of the respective intensities; and generating a two-dimensional image of the respective intensities of the first acoustic field in the region.

There is further provided, in accordance with some applications of the present invention, apparatus for assessing a characteristic of an acoustic field in a region of a medium, the apparatus including:

a first acoustic transducer configured to transmit a first acoustic field at a first frequency into the region, the first acoustic field generating oscillatory motion at the first frequency of scatterers disposed in the region, each scatterer oscillating around a respective equilibrium position;

a second acoustic transducer configured to:

(a) transmit first and second acoustic pulses into the region, each pulse having a center frequency that is higher than the first frequency, and the time interval between the pulses being n+0.5 times the period of the first acoustic field, n being a positive integer; and (b) receive respective echoes of each pulse scattering off an oscillating scatterer in the region, the first and second pulses being synchronized with the first acoustic field such that the first pulse scatters off the oscillating scatterer when the oscillating scatterer is at a first displacement extremum with respect to the equilibrium position, and the second pulse scatters off the oscillating scatterer when the oscillating scatterer is at a second displacement extremum that is opposite the first displacement extremum with respect to the equilibrium position; and a computer processor configured to:

(a) extract a time shift between the received echoes that is due to motion of the oscillating scatterer, (b) based on the extracted time shift, calculate a displacement amplitude of the oscillating scatterer, and (c) output an indication of the displacement amplitude of the oscillating scatterer.

For some applications, the second acoustic transducer is configured to transmit the first and second acoustic pulses into the region, each pulse having a center frequency that is 5 to 50 times higher than the first frequency.

For some applications, the computer processor is further configured to derive at least one parameter of the first acoustic field from the displacement amplitude and output an indication of the parameter.

For some applications, the at least one parameter is a velocity amplitude of the oscillating scatterer.

For some applications, the computer processor is further configured to derive an intensity of the acoustic field based on the velocity amplitude, and to output an indication of the intensity.

For some applications, the second acoustic transducer is configured to transmit the first and second acoustic pulses into the region, the time interval between the pulses being n+0.5 times the period of the first acoustic field, and n being a positive integer less than or equal to 1000.

For some applications, the second acoustic transducer is configured to transmit the first and second acoustic pulses into the region, the time interval between the pulses being n+0.5 times the period of the first acoustic field, and n being a positive integer greater than or equal to 5.

For some applications, the first acoustic transducer is configured to transmit the first acoustic field into the region by transmitting high intensity focused ultrasound (HIFU) energy at the first frequency into the region.

For some applications, the first acoustic transducer is configured to transmit the HIFU energy at the first frequency, the first frequency being 0.1-5 MHz.

For some applications, the apparatus further includes a single housing to which the first and second acoustic transducers are coupled, wherein the housing aligns the first acoustic field and the pulses to be parallel or anti-parallel, i.e., the housing aligns the axis of the first acoustic field and the direction of propagation of the pulses to be parallel or anti-parallel.

For some applications:

the second acoustic transducer is configured to:
- (a) transmit a plurality of pairs of first and second acoustic pulses into the region in a plurality of respective directions, each pulse having a center frequency that is higher than the first frequency, and the time interval between respective first and second pulses being n+0.5 times the period of the first acoustic field, and
- (b) receive respective echoes of each pulse scattering off a respective oscillating scatterer in the region,
  each pair of first and second pulses being synchronized with the first acoustic field such that the first pulses scatter off the respective oscillating scatterers when the oscillating scatterers are at respective first displacement extrema with respect to respective equilibrium positions, and the second pulses scatter off the respective oscillating scatterers when the oscillating scatterers are at respective second displacement extrema that are opposite the respective first displacement extrema with respect to the respective equilibrium positions; and the computer processor is configured to:
- (a) extract respective time shifts between respective pairs of received echoes that are due to motion of the respective oscillating scatterers,
- (b) based on the extracted time shifts, calculate respective displacement amplitudes of the respective oscillating scatterers,
- (c) output respective indications of the respective displacement amplitudes of the respective oscillating scatterers, and
- (d) generate a two-dimensional image of the respective displacement amplitudes in the region.

For some applications, the computer processor is further configured to:

based on the displacement amplitudes, calculate respective velocity amplitudes of the respective oscillating scatterers;

output respective indications of the respective velocity amplitudes of the respective oscillating scatterers; and generate a two-dimensional image of the respective velocity amplitudes in the region.

For some applications, the computer processor is further configured to:

based on the velocity amplitudes, calculate respective intensities of the first acoustic field;

output respective indications of the respective intensities; and generate a two-dimensional image of the respective intensities of the first acoustic field in the region.

There is further provided, in accordance with some applications of the present invention, a method for assessing a characteristic of an acoustic field in a region of a medium, the method including:

driving a first acoustic transducer to transmit a first acoustic field at a first frequency into the region, the first acoustic field generating oscillatory motion at the first frequency of scatterers disposed in the region, each scatterer oscillating around a respective equilibrium position;

driving a second acoustic transducer to:
- (a) transmit at least 5 acoustic pulses into the region, each pulse having a center frequency that is higher than the first frequency, and
- (b) receive respective echoes of each pulse scattering off an oscillating scatterer in the region; and using at least one computer processor:
- (a) extracting a series of time shifts, each time shift being between any two of the received echoes, that are due to motion of the oscillating scatterer,
- (b) based on the extracted time shifts, estimating a series of respective displacements of the oscillating scatterer,
- (c) based on the calculated displacements, statistically deriving a displacement amplitude of the oscillating scatterer, and
- (d) driving an output device to output an indication of the displacement amplitude of the oscillating scatterer.

For some applications, extracting a series of time shifts includes extracting a series of time shifts wherein each time shift is between two successive received echoes.

For some applications, extracting a series of time shifts includes selecting two of the received echoes between which is the largest time shift.

For some applications, driving the second acoustic transducer includes driving the second acoustic transducer to transmit at least 5 acoustic pulses into the region, each pulse having a center frequency that is 5 to 50 times higher than the first frequency.

For some applications, driving the second acoustic transducer includes driving the second acoustic transducer to transmit less than 50 acoustic pulses into the region.

For some applications, using at least one computer processor further includes:

deriving at least one parameter of the first acoustic field from the displacement amplitude of the oscillating scatterer; and driving the output device to output an indication of the parameter.

For some applications, deriving the at least one parameter of the first acoustic field includes, based on the displacement amplitude, calculating a velocity amplitude of the oscillating scatterer.

For some applications, deriving the at least one parameter of the first acoustic field includes, based on the velocity amplitude, calculating an intensity of the first acoustic field at a location of the oscillating scatterer.

For some applications, driving the first acoustic transducer to transmit the first acoustic field includes driving a first acoustic transducer to transmit high intensity focused ultrasound (HIFU) energy at the first frequency into the region.

For some applications, driving the first acoustic transducer to transmit the HIFU energy includes driving the first acoustic transducer to transmit the HIFU energy at the first frequency, the first frequency being 0.1-5 MHz.

There is further provided, in accordance with some applications of the present invention, apparatus for assessing a characteristic of an acoustic field in a region of a medium, the apparatus including:

a first acoustic transducer configured to transmit a first acoustic field at a first frequency into the region, the first acoustic field generating oscillatory motion at the first frequency of scatterers disposed in the region, each scatterer oscillating around a respective equilibrium position;

a second acoustic transducer configured to:

(a) transmit at least 5 acoustic pulses into the region, each pulse having a center frequency that is higher than the first frequency, and (b) receive respective echoes of each pulse scattering off an oscillating scatterer in the region; and a computer processor configured to:

(a) extract a series of time shifts, each time shift being between any two of the received echoes, that are due to motion of the oscillating scatterer, (b) based on the extracted time shifts, estimate a series of respective displacements of the oscillating scatterer, (c) based on the calculated displacements, statistically derive a displacement amplitude of the oscillating scatterer, and (d) output an indication of the displacement amplitude of the oscillating scatterer.

For some applications, the computer processor is configured to extract the series of time shifts, wherein each time shift is between two successive received echoes.

For some applications, the second acoustic transducer is configured to transmit the first and second acoustic pulses into the region, each pulse having a center frequency that is 5 to 50 times higher than the first frequency.

For some applications, the computer processor is further configured to derive at least one parameter of the first acoustic field from the displacement amplitude and output an indication of the parameter.

For some applications, the at least one parameter is a velocity amplitude of the oscillating scatterer.

For some applications, the computer processor is further configured to derive an intensity of the acoustic field based on the velocity amplitude, and to output an indication of the intensity.

For some applications, the first acoustic transducer is configured to transmit the first acoustic field into the region by transmitting high intensity focused ultrasound (HIFU) energy at the first frequency into the region.

For some applications, the first acoustic transducer is configured to transmit the HIFU energy at the first frequency, the first frequency being 0.1-5 MHz.

For some applications, the apparatus further includes a single housing to which the first and second acoustic transducers are coupled, wherein the housing aligns the first acoustic field and the acoustic pulses to be parallel or anti-parallel.

There is further provided, in accordance with some applications of the present invention, apparatus for use with a focal region of high intensity focused ultrasound (HIFU) energy, the apparatus including:

a first ultrasound transducer configured to transmit a first acoustic field by emitting the HIFU energy into a region of a medium at a first frequency, the first acoustic field generating oscillatory motion at the first frequency of scatterers disposed in the region, each scatterer oscillating around a respective equilibrium position;

an acoustic probe, wherein the acoustic probe is configured to emit pulse-echo ultrasound energy into the medium at an imaging frequency, and wherein an acoustic element selected from the group consisting of the first ultrasound transducer, a second ultrasound transducer, and the acoustic probe is configured to (i) transmit first and second acoustic pulses into the region, each pulse having a center frequency that is higher than the first frequency, and the time interval between the pulses being n+0.5 times the period of the first acoustic field, n being a positive integer, and (ii) receive respective echoes of each pulse scattering off an oscillating scatterer in the region, the first and second pulses being synchronized with the first acoustic field such that the first pulse scatters off the oscillating scatterer when the oscillating scatterer is at a first displacement extremum with respect to the equilibrium position, and the second pulse scatters off the oscillating scatterer when the oscillating scatterer is at a second displacement extremum that is opposite the first displacement extremum with respect to the equilibrium position; and a computer processor configured to (a) generate a real-time sonogram of the medium based on reflections of the pulse-echo ultrasound energy that is transmitted by the acoustic probe, (b) extract a time shift between the received echoes that is due to motion of the oscillating scatterer, (c) based on the extracted time shift, calculate a displacement amplitude of the oscillating scatterer, and (d) generate a map of displacement amplitudes on a portion of the sonogram corresponding to the region.

For some applications, the acoustic element includes the second ultrasound transducer.

For some applications, the acoustic element includes the acoustic probe.

For some applications, the acoustic element includes the first ultrasound transducer.

For some applications, the first frequency is 0.1-5 MHz.

For some applications, the center frequency of each pulse is at least 5 to 50 higher than the first frequency.

For some applications, the imaging frequency is 1-50 MHz.

For some applications, the computer processor is further configured to (a) based on the displacement amplitude, calculate a velocity amplitude of the first acoustic field in the region, and (b) generate a map of velocity amplitudes on a portion of the sonogram corresponding to the region.

For some applications, the computer processor is further configured to (a) based on the velocity amplitude, calculate an intensity of the first acoustic field in the region, and (b) generate a map of intensities of the first acoustic field on a portion of the sonogram corresponding to the region.

For some applications, the medium is tissue of a body of a subject and wherein the first ultrasound transducer is configured to cause a therapeutic effect in the tissue by emitting the HIFU energy into the tissue.

For some applications, the oscillating scatterer is an inhomogeneity in the tissue.

For some applications, the first ultrasound transducer is configured to cause the therapeutic effect in the tissue by heating the tissue.

For some applications, the computer processor is further configured to monitor a change in a mechanical property of the tissue by monitoring a time variation of the displacement amplitude; and in response to the monitoring, terminating the first acoustic field when the mechanical property of the tissue reaches a threshold value.

For some applications, the mechanical property of the tissue is mechanical impedance of the tissue, and wherein the computer processor is configured to (a) monitor a change in the mechanical impedance of the tissue by monitoring a time variation of the displacement amplitude, and (b) in response to the monitoring, terminate the first acoustic field when the mechanical impedance of the tissue reaches a threshold value.

For some applications, the computer processor is configured to monitor the change in the characteristic over a time period that is 1-120 seconds long.

For some applications:

the first ultrasound transducer is configured to operate in distinct calibration and therapy modes to facilitate application of therapeutic HIFU energy to a target location, in each of the modes emitting the HIFU energy with one or more differing respective parameters, and the computer processor is configured to vary the one or more respective parameters such that when the first ultrasound transducer operates in the therapeutic mode the HIFU energy causes a therapeutic effect in the tissue whereas when the first ultrasound transducer is operating in the calibration mode the HIFU energy does not cause a therapeutic effect in the tissue.

For some applications, the computer processor is configured to vary a duration of a HIFU-pulse of the HIFU energy, such that when the first ultrasound transducer operates in the therapeutic mode the duration of the HIFU-pulse is longer than the duration of the HIFU-pulse is when the first ultrasound transducer operates in the calibration mode.

For some applications, the computer processor is configured to vary a duty-cycle of the HIFU energy, such that when the first ultrasound transducer operates in the therapeutic mode the duty-cycle is higher than the duty-cycle is when the first ultrasound transducer operates in the calibration mode.

For some applications, the computer processor is configured to vary a power of the HIFU energy, such that when the first ultrasound transducer operates in the therapeutic mode the power of the HIFU energy is higher than the power of the HIFU energy is when the first ultrasound transducer operates in the calibration mode.

For some applications, the computer processor is configured to monitor the tissue when the first ultrasound transducer operates in the therapeutic mode and to vary the parameters of the therapeutic mode according to the monitoring in order to alter an effect on the tissue.

For some applications, the apparatus includes a targeting unit configured to move the focal region of the HIFU energy when the first ultrasound transducer operates in the calibration mode.

For some applications, the targeting unit is configured such that manual movement of the targeting unit moves the focal region of the HIFU energy within the medium by moving the first ultrasound transducer with respect to the medium.

For some applications, the targeting unit includes (i) a first-transducer controller and (ii) targeting circuitry configured to (a) obtain data corresponding to the focal region of the HIFU energy on a map selected from the group consisting of: the map of displacement amplitudes, the map of velocity amplitudes, and the map of intensities, (b) obtain data corresponding to a target location in the medium, and (c) send an electric signal to the first-transducer controller, wherein the first-transducer controller is configured to receive the electric signal and in response thereto move the focal region of the HIFU energy toward the target location within the medium.

For some applications, the first-transducer controller is configured to (a) move the focal region of the HIFU energy with respect to the first ultrasound transducer, and (b) change a size of the focal region of the HIFU energy by applying phased-array control to the HIFU energy emitted by the first ultrasound transducer.

For some applications, the first-transducer controller is configured to move the focal region of the HIFU energy by moving the first ultrasound transducer with respect to the medium.

For some applications, the apparatus further includes a single housing to which the first ultrasound transducer and the acoustic element are coupled, wherein the housing aligns the first acoustic field and the acoustic pulses to be parallel or anti-parallel.

The present invention will be more fully understood from the following detailed description of applications thereof, taken together with the drawings, in which:

DETAILED DESCRIPTION

Figure 1B:
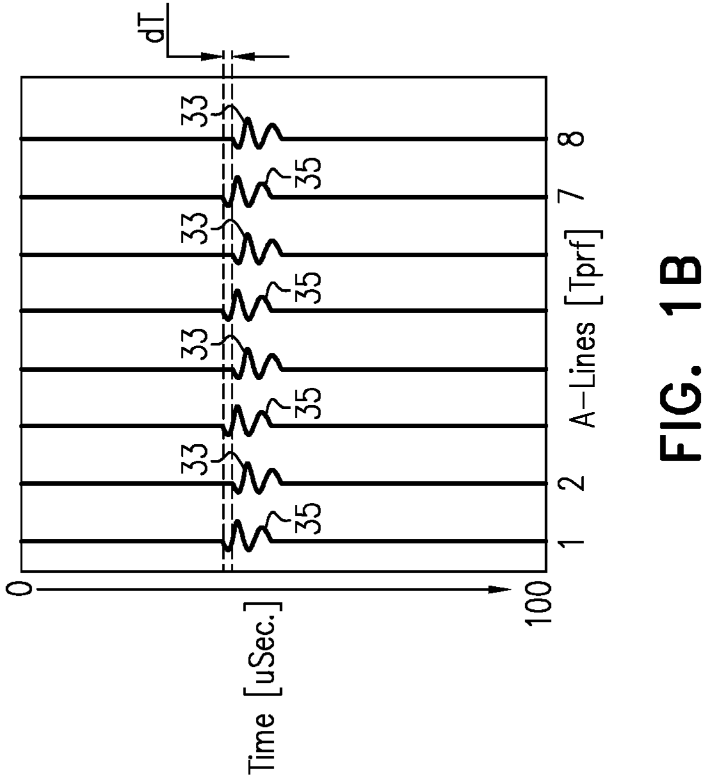
FIG. 1B is a graph showing multiple A-lines on the x-axis and the time at which each respective echo was received by the second transducer on the y-axis.

An acoustic field propagating in a medium generates oscillatory motion of particles, or scatterers, within the medium, a phenomenon known as the particle-velocity of the acoustic field. The oscillations occur at the frequency of the acoustic field. The intensity of the acoustic field relates to (a) pressure p and (b) particle-velocity u. In harmonic fields, with frequency f, particle-velocity amplitude U is related to displacement amplitude D, as shown hereinbelow in Equation 8. Pressure and particle-velocity are related through the mechanical impedance of the medium, by the equation $Z=p/u$. Therefore, assuming a medium of constant mechanical impedance Z, the displacement amplitude and the velocity amplitude of the oscillating scatterers in a region of higher intensity are higher than the displacement amplitude and velocity amplitude of the oscillating scatterers are in a region of lower intensity, i.e., in regions with constant mechanical impedance Z, the particle-velocity of the acoustic field is highest in the region of highest intensity within the field.

Intensity of an acoustic field is the product of pressure p and particle-velocity u, as given by the following equation:

$$I(t)=p(t)u(t), \quad \text{[Equation 1]}$$

where I is the instantaneous intensity at some position in space, p is the pressure, and u is the particle-velocity at that position.

The local complex mechanical impedance Z of the medium is defined by:

$$Z=p/u, \quad \text{[Equation 2]}$$

where p and u are the complex amplitudes of harmonic waves of pressure and particle-velocity correspondingly, at a specific frequency. Mechanical impedance Z is a characteristic of the medium, and it may be position-dependent and frequency-dependent. An illustrative example, utilizing numbers that are close to those of therapeutic ultrasound, is as follows:

Z=1.5 MRayl.,
pressure amplitude p=1.5 MPa, and therefore
particle-velocity amplitude u=1.5 [MPa]/1.5 [MRayl.]=1 [m/s].

The time-averaged intensity of the acoustic field can be written in the form:

$$I=p\hat{}2/(2Z), \quad \text{[Equation 3]}$$

providing intensity I in terms of pressure amplitude p. Equivalently, pressure p can be substituted in Equation 3 by the product of impedance Z and particle-velocity u to derive $$I=Zu\hat{}2/2, \quad \text{[Equation 4]}$$

which gives intensity I in terms of particle-velocity u.

Particle-velocity u is a function of intensity I and impedance Z, as given by the following equation:

$$u=\mathrm{sqrt}(2I/Z), \quad \text{[Equation 5]}$$

thus, for a given intensity I, changes in impedance Z will result in a change in particle-velocity u.

The position z(t) of the oscillating scatterer at a given point in time t may be written in the form:

$$z(t)=z0+D\cos(2pi\, ft+\mathrm{phi}), \quad \text{[Equation 6]}$$

where z0 is the equilibrium position of the scatterer, D is the displacement amplitude measured from the equilibrium position, phi is phase, and f is the frequency of the acoustic field.

In harmonic fields, with frequency f, particle velocity u(t) may be written in the form:

$$u(t)=U\sin(2pi\, f\, t+\mathrm{phi2}), \quad \text{[Equation 7]}$$

where U is the particle-velocity amplitude U.

Particle velocity amplitude U is related to displacement amplitude D, as given by the following equation:

$$U=2pi\, f\, D. \quad \text{[Equation 8]}$$

Figure 1A:
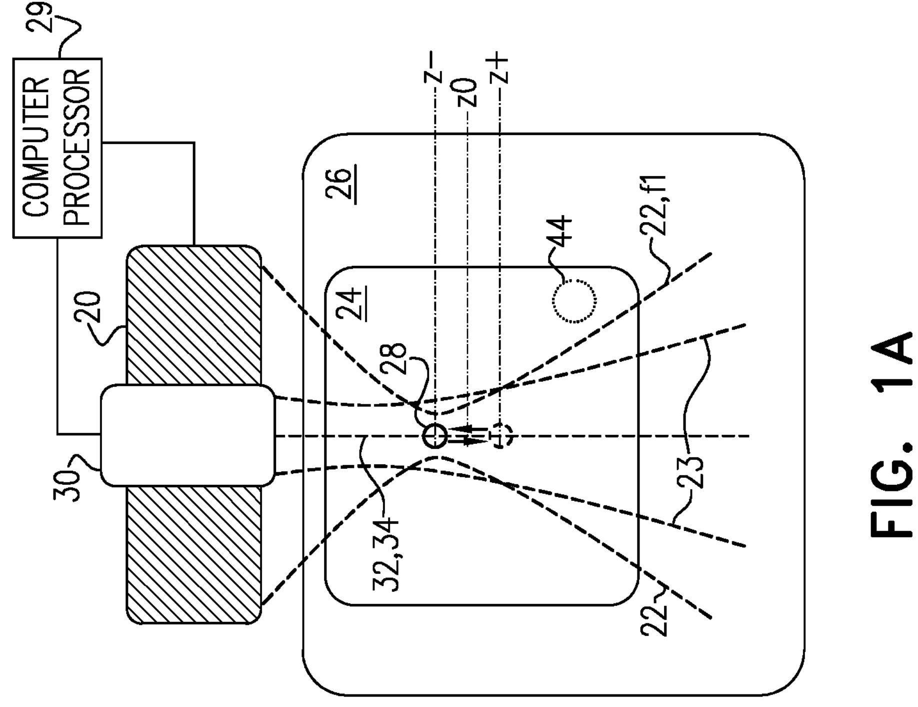
FIG. 1A is a schematic illustration of a first acoustic transducer transmitting a first acoustic field into a region, an oscillating scatterer in the region, and a second acoustic transducer transmitting acoustic pulses toward the oscillating particle, in accordance with some applications of the present invention.

Reference is now made to FIG. 1A, which is a schematic illustration of first acoustic transducer 20 transmitting a first acoustic field 22 into a region 24 of a medium 26, an oscillating scatterer 28 in region 24, and a second acoustic transducer 30 transmitting a diagnostic field 23 into the region and transmitting acoustic pulses toward oscillating scatterer 28, in accordance with some applications of the present invention. First acoustic transducer 20 and second acoustic transducer 30 may be coupled to a single housing, such as housing 42 in FIG. 5, that aligns first acoustic field 22 and the acoustic pulses to be parallel or anti-parallel, i.e., housing 42 aligns the axis of first acoustic field 22 and the direction of propagation of the acoustic pulses to be parallel or anti-parallel. First acoustic transducer 20 transmits first acoustic field 22, e.g., by emitting high intensity focused ultrasound (HIFU) energy, into region 24 at a first frequency f1, which is typically at least 0.1 MHz and/or less than 5 MHz. First acoustic field 22 may be, for example, a focused field with a focal point or focal volume positioned some distance in front of the transducer. First acoustic field 22 generates oscillatory motion of scatterers, such as scatterer 28, disposed in region 24. The oscillations of the scatterers is the particle-velocity of first acoustic field 22, and is a fundamental characteristic of the acoustic field. The scatterers oscillate at first frequency f1, each scatterer oscillating around a respective equilibrium position, such as equilibrium position z0 shown in FIG. 2.

Figure 2:
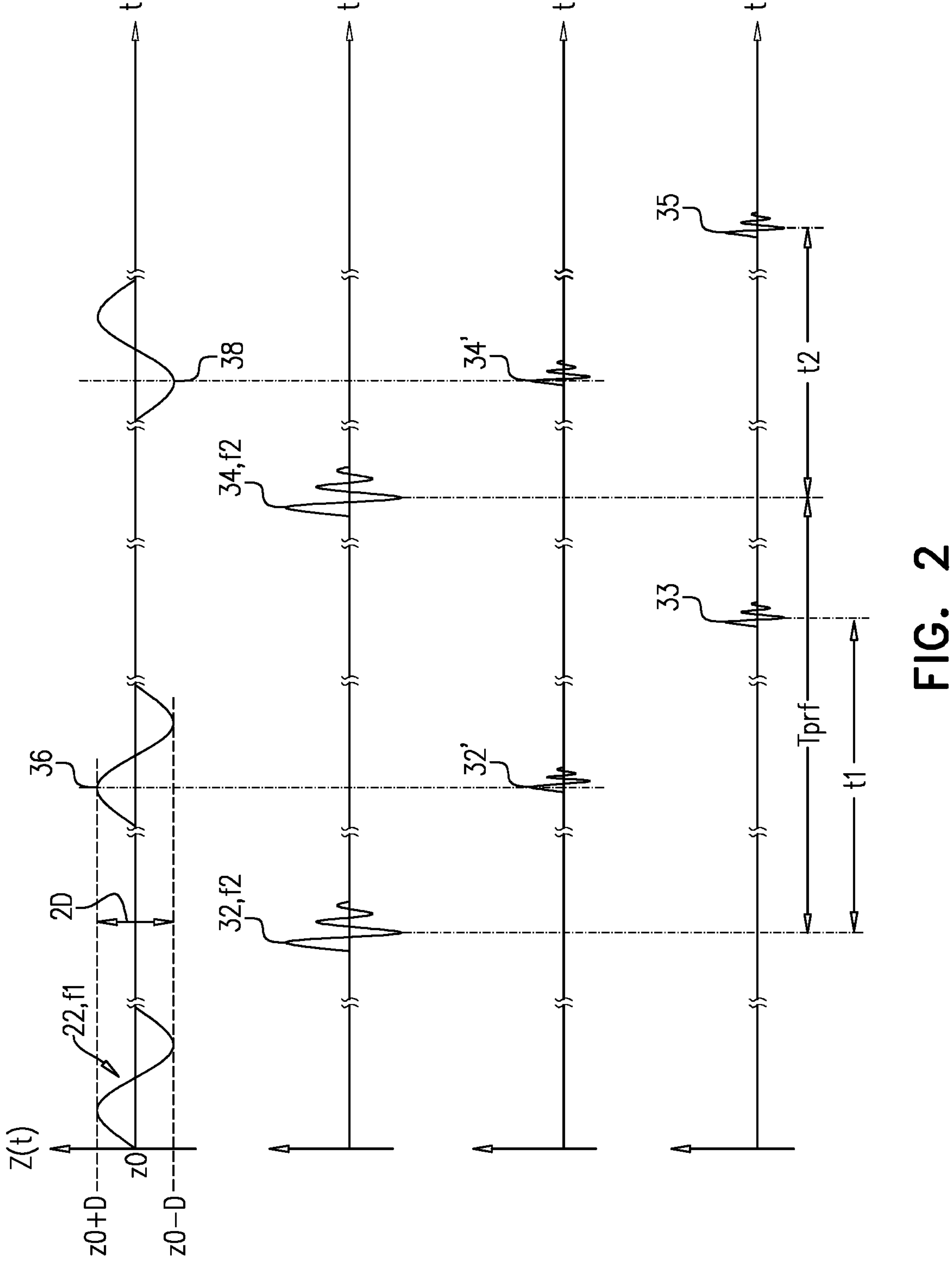
FIG. 2 is a schematic illustration of synchronization between the acoustic pulses and the first acoustic field, in accordance with some applications of the present invention.

For some applications, second acoustic transducer 30 generates A-lines by transmitting acoustic pulses into region 24, such as first acoustic pulse 32 and second acoustic pulse 34 shown in FIG. 2. First and second acoustic pulses 32 and 34 each have a center frequency f2 that is higher than first frequency f1, e.g., at least 5 and/or less than 50 times higher than first frequency f1. The time interval between successive A-lines, e.g., the time interval between first acoustic pulse 32 and second acoustic pulse 34, is n+0.5 times the period T1 of first acoustic field 22, where n is a positive integer. Setting the time interval to be n+0.5 times period T1 means the scatterer will perform exactly n+0.5 oscillations between the A-lines. If first acoustic pulse 32 and second acoustic pulse 34 are synchronized with first acoustic field 22, as further described hereinbelow with respect to FIG. 2, then each pulse will scatter off scatterer 28 when scatterer 28 is either at a maximum negative position z− in its trajectory or at a maximum positive position z+ in its trajectory.

Reference is now made to FIG. 1B, which is a graph showing multiple A-lines on the x-axis and the time at which each respective echo was received by the second transducer on the y-axis. Synchronization with first acoustic field 22, as further described hereinbelow with respect to FIG. 2, enables receiving a first echo from first pulse 32 scattering off scatterer 28 at maximum negative position z−, and a second echo from second pulse 34 scattering off scatterer 28 at maximum positive position z+. By way of example, 8 A-lines are shown on the graph, with equal time intervals Tprf between them, Tprf being equal to n+0.5 times period T1. Due to the synchronization, echoes 35 from A-lines 1, 3, 5, and 7 are received from an acoustic pulse scattering off scatterer 28 at z−, and echoes 33 from A-lines 2, 4, 6, and 8 are received from an acoustic pulse scattering off scatterer 28 at z+. The respective received echoes from each A-line are plotted against time on the y-axis, representing the time at which each respective echo is received, each time measured with respect to the time each respective pulse was transmitted. A time shift dT between successive echoes emerges. The time scale of 1-100 microseconds is shown as an arbitrary example.

Reference is now made to FIG. 2, which is a schematic illustration of synchronization between the acoustic pulses and first acoustic field 22, in accordance with some applications of the present invention. During the oscillations of each scatterer under influence of first acoustic field 22, each scatterer reaches a maximum positive displacement z0+D from equilibrium position z0 and a maximum negative displacement z0-D from equilibrium position z0. The total displacement of each oscillating scatterer is therefore equal to 2D. The oscillations are consistent in time and would appear as a continuous sine wave when displacement Z(t) is plotted against time (t); however, for the purpose of clearly showing synchronization, as described hereinbelow, only a few distinct periods of the oscillation appear in FIG. 2.

First pulse 32 and second pulse 34 may be synchronized with first acoustic field 22 such that (a) first pulse 32 scatters off an oscillating scatterer, such as scatterer 28 in FIG. 1A, when scatterer 28 is at a first displacement extremum 36, e.g., maximum positive displacement +D, with respect to equilibrium position z0, and (b) second pulse scatters off scatterer 28 when scatterer 28 is at a second displacement extremum 38 that is opposite the first displacement extremum, e.g., maximum negative displacement−D, with respect to equilibrium position z0. Pulse 32' represents first acoustic pulse 32 scattering off scatterer 28 when scatterer 28 is located at first displacement extremum 36. Pulse 34' represents second acoustic pulse 34 scattering off scatterer 28 when scatterer 28 is located at second displacement extremum 38. Echo 33 is the echo received from first acoustic pulse 32, and echo 35 is the echo received from second acoustic pulse 34.

Time interval Tprf between first and second acoustic pulses 32 and 34 is limited by a desired penetration depth. Between each transmitted pulse there must be at least enough time for the first transmitted pulse to reach the penetration depth, scatter off the scatterer, and for the echo to be received. For example, Tprf is likely to be at least 100 microseconds, i.e., the A-lines are pulsed at a PRF of less than 10 kHz, while first frequency f1 of first acoustic field 22 may be as high as 5 MHz. Therefore scatterer 28 may exhibit hundreds of oscillations between each A-line. Synchronizing the pulses with first acoustic field 22, as described hereinabove, allows the scatterer to perform n+0.5 oscillations while still ensuring that each echo is received from the scatterer when it is at a displacement extremum. The synchronization includes (a) setting the time intervals Tprf to be n+0.5 times period T1, as well as (b) synchronizing the pulses with the phase of oscillations to ensure that after the n+0.5 oscillations the scatterer is at an extremum of its displacement and not, for example, at equilibrium position z0.

The result is that between each pair of received echoes, scatterer 28 undergoes a total displacement of 2D. Echo 33 is received at time t1 after the transmission of first acoustic pulse 32, and echo 35 is received at time t2 after the transmission of second acoustic pulse 34. Time shift dT is equal to t2−t1 and is related to displacement 2D of the scatterer. At least one computer processor 29 is used to extract time shift dT between the received echoes and based on extracted time shift dT, calculate displacement amplitude D of oscillating scatterer 28, which is related to the local particle velocity (Equation 8), and therefore to the local intensity of first acoustic field 22 at the location of the oscillating scatterer (Equation 4). The location of oscillating scatterer 28 refers to a location in region 24 that includes the entire space over which the oscillating scatterer is oscillating. Computer processor 29 outputs, or drives an output device such as output device 40 shown in FIG. 4 to output, an indication of the displacement amplitude D of oscillating scatterer 28.

Displacement D may be used to derive at least one parameter of first acoustic field 22, such as velocity amplitude. Based on the displacement amplitude D, computer processor 29 may use Equation 7 to calculate a velocity amplitude of oscillating scatterer 28. Knowing the mechanical impedance of the medium, computer processor 29 may also use Equation 4 to calculate intensity of first acoustic field 22 at the location of oscillating scatterer 28, or use Equation 2 to calculate pressure of first acoustic field 22 at the location of oscillating scatterer 28. If a pressure amplitude at the location of oscillating scatterer 28 is known, then computer processor 29 may use Equation 2 to calculate the mechanical impedance of the medium at the location of oscillating scatterer 28. Computer processor 29 outputs, or drives an output device such as output device 40, to output indications of the abovementioned parameters of first acoustic field 22, e.g., velocity amplitude, intensity, and mechanical impedance in terms of root-mean-squared value, variance, maximum value, peak-to-peak value, amplitude, and/or phase.

For some applications, second acoustic transducer 30 transmits a plurality of pairs of first and second acoustic pulses 32 and 34 in a plurality of respective directions in region 24, and receives respective echoes of each pulse scattering off respective oscillating scatterers. Each pair of pulses is synchronized with first acoustic field 22 as described hereinabove. Computer processor 29 extracts respective time shifts dT between respective pairs of received echoes 33 and 35. Based on the extracted time shifts, computer processor 29 may calculate respective displacement amplitudes D of the respective oscillating scatterers, and output, or drive an output device to output, respective indications of the respective displacement amplitudes, and generate a two-dimensional image, e.g., a map, of the respective displacement amplitudes in the region.

As described hereinabove, respective velocity amplitudes of the respective oscillating scatterers may be calculated based on the respective displacement amplitudes, and respective intensities of first acoustic field 22 in the region may be calculated based on the respective velocity amplitudes. Computer processor 29 can output, or drive an output device to output, respective indications of the velocity amplitudes and intensities, and generate respective two-dimensional images, e.g., respective maps, of the respective velocity amplitudes in the region and the respective intensities of first acoustic field 22 in the region.

Figure 4:
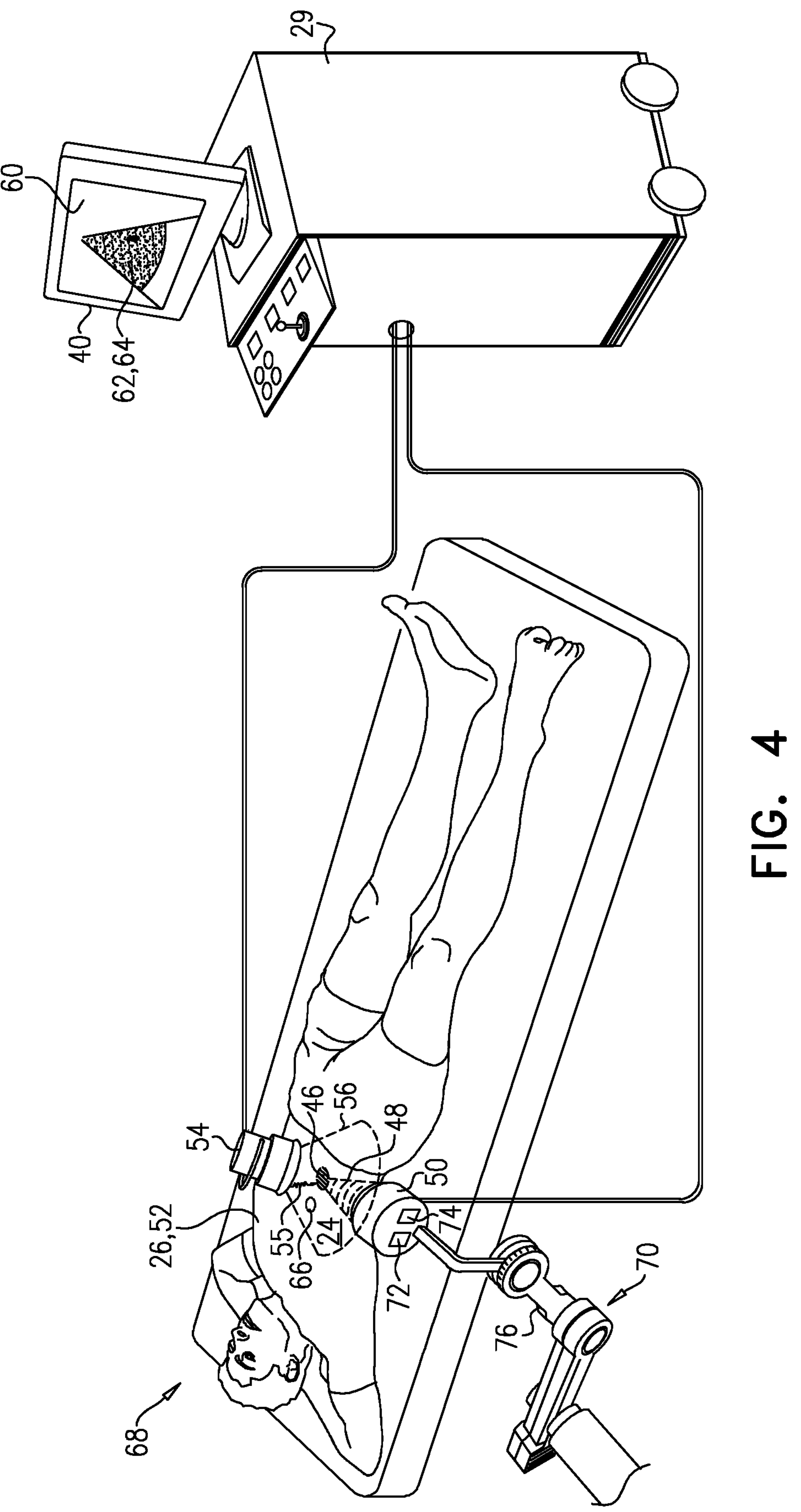
FIG. 4 is a schematic illustration of a high intensity focused ultrasound (HIFU) transducer and an acoustic probe both placed against skin of a subject, according to some applications of the present invention.

For some applications, second acoustic transducer 30 may be, for example, a linear array probe, a convex array probe, a phased array probe, or any other standard design for a diagnostic probe that is configured for beam-forming and pulse-echo operation, including color-Doppler imaging. Computer processor 29 is configured to work in pulse-echo mode and to perform beam forming techniques in order to acquire the echo data from a specific location in medium 26. Usually, the same array of piezoelectric elements is used for generating a sonogram and the respective maps of first acoustic field 22: first, the sonogram is generated using pulse-echo ultrasound at an imaging frequency, and then, the respective maps are generated as described hereinabove. The sonogram provides guidance capabilities. For example, a target location 44, e.g., a tumor, can be seen on the sonogram, and the focal region of first acoustic field 22 can be seen on the map. When fused into one image, real-time feedback of the location of the focal region with respect to target location 44 is provided. A targeting unit, such as is shown in FIG. 4 may be used to move the focal region to target location 44.

It is noted that apparatus may be sold including second acoustic transducer 30 and computer processor 29 but not first acoustic transducer 20. Such apparatus would have all the same properties as described above. In such a case, second acoustic transducer 30 together with computer processor 29 may be used to assess a characteristic, e.g., displacement amplitude, or particle-velocity, of an already-existing first acoustic field.

For some applications, displacement amplitude D of oscillating scatterer 28 may be obtained without synchronization of the acoustic pulses with first acoustic field 22. Second acoustic transducer 30 may transmit at least 5 acoustic pulses, e.g., less than 50 acoustic pulses, into region 24. Each pulse has a center frequency that is at least 5 and/or less than 50 times higher than first frequency f1 of first acoustic field 22. Respective echoes of each pulse scattering off an oscillating scatterer, such as scatterer 28, are received by second acoustic transducer 30. Computer processor 29 extracts a series of time shifts. Each individual time shift in the series does not have to be between two successive echoes, rather each time shift can be between any two of the received echoes. For example, if 5 echoes are received, then a total of 10 time shifts dT can be extracted, e.g., between echoes 1 and 2, 2 and 3, 3 and 4, 4 and 5, 1 and 3, 1 and 4, 1 and 5, 2 and 4, 2 and 5, and 3 and 5. For some applications, computer processor 29 selects two of the received echoes between which is the largest time shift.

A series of respective displacement amplitudes of scatterer 28 may be estimated based on the extracted series of time shifts, and then statistical analysis is used to derive the displacement amplitude of oscillating scatterer 28. Once the displacement amplitude is derived computer processor 29 outputs, or drives an output device to output, an indication of the displacement amplitude. As described hereinabove, once the displacement amplitude of the oscillation has been obtained, the velocity amplitude of the oscillation, and intensity at the location of the scatterer may be calculated, and respective maps of first acoustic field 22 generated.

Standard algorithms, such as autocorrelation for phase-detection as described in the abovementioned Kasai reference, describe the calculation of an assumed constant flow velocity from a derived phase shift, using the equation $$v=c\ \mathrm{phi}(T)/(4pi\ f\ T),$$

which gives the parallel component of the velocity in terms of the phase phi(T) that is acquired during the time T, where T is the time between successive A-Lines (Tprf), and f is the center frequency of the pulse. In the case of particle-velocity, however, velocity is not constant over the time interval between successive A-lines. Therefore, in accordance with some applications of the present invention, the displacement amplitude D is calculated using:

$$2D=c\ \mathrm{phi}(T)/(4pi\ f),$$

and the particle-velocity amplitude U is calculated using:

$$U=2pi\ f1D=c\ \mathrm{phi}(T)f1/(4f),$$

where f1 is the frequency of the first acoustic field 22.

Similarly, cross-correlation algorithms, such as described in the above mentioned Bonnefous reference, usually derive the time shift dT and use it to estimate an assumed constant velocity by:

$$v=c\ dT/(2T).$$

In the case of particle-velocity, the time shift is used to derive displacement amplitude D by:

$$D=c\ dT/2,$$

and the particle-velocity amplitude U by:

$$U=2pi\ f1D.$$

Figure 3B:
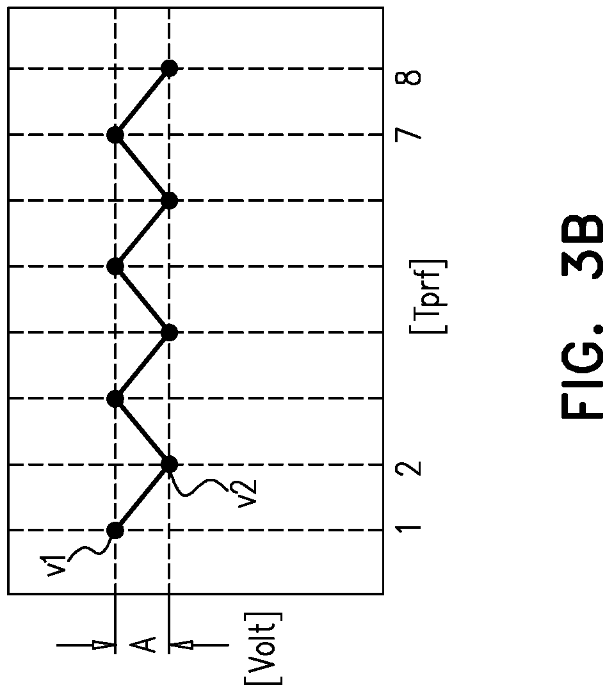
FIG. 3B is a graph showing measurements of signal values at a specific sample point along successive A-lines, in accordance with some applications of the present invention.
Figure 3A:
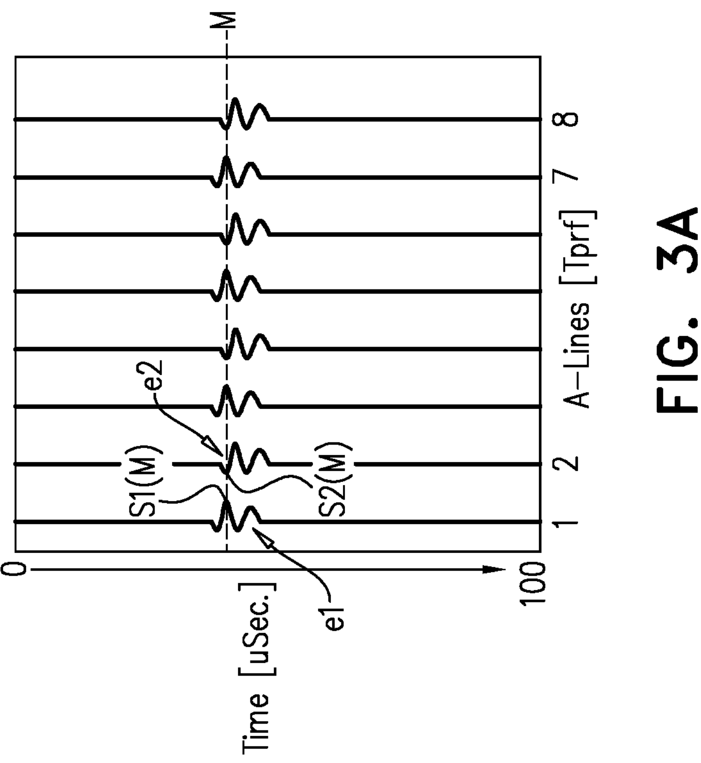
FIG. 3A is a graph showing eight A-lines and with respective echoes shown on the A-lines, in accordance with some applications of the present invention.

Reference is now made to FIG. 3A, which is a graph showing 8 A-lines and with respective echoes shown on the A-lines, and FIG. 3B, which is a graph showing the value of a received signal Sk(n) for a specific sample point n across successive A-lines, where k is the index number of the A-line, in accordance with some applications of the present invention. For example, a sample point number 700 on the second A-line is written as S2(700), and the same sample point on the third A-line is written as S3(700). The index n can have values of from 0 to N−1, where N is the total number of sample points in the A-line. FIG. 3A shows 8 successive A-lines, all transmitted from the same direction but at different times, with time interval Tprf between each pair of lines being constant. By way of example, the length of each A-line is 100 microseconds and the sampling frequency for each A-line is 100 MHz; therefore, there are 10 nanoseconds between samples along each A-line and a total of 10,000 sample points on each A-line. An echo is detected on each A-line from a single scatterer, such as scatterer 28, that exhibits oscillations in space. The pulses are synchronized with first acoustic field 22, as described hereinabove, so that odd echoes are received from the scatterer at maximum negative position z- and even echoes are received from the scatterer at maximum positive position z+. Accordingly, the respective times of the received echoes alternate back and forth, with a time shift dT emerging that is related to the total displacement 2D of oscillating scatterer 28. The dashed horizontal line N in FIG. 3A represents a specific sample point number n=M across the successive A-lines, the value of M representing a specific depth in medium 26. S1(M) is the sample point number M on the first A-line, and S2(M) is the same sample point number M on the second A-line. The graph in FIG. 3B shows the variation of the signal value of sample point number M over successive A-lines. As can be seen in FIG. 3A, S1(M) is at a maximum on the echo e1 on the first A-line, and S2(M) is at a minimum on the echo e2 on the second A-line. Correspondingly, as shown in FIG. 3B, signal value v1 of sample point S1(M) is at a maximum value and signal value v2 of sample point S2(M) is at a minimum value. Across the successive A-lines, the sampling point number M on the odd-numbered A-lines all have approximately the same value, and the sampling point number M on the even-numbered A-lines all have approximately the same value (that is different from the value on the odd-numbered A-lines). An amplitude A of the variation of the signal from the same sample point across the successive A-lines is related to displacement amplitude D of oscillating scatterer 28, and can be written in the form:

$$A=2\ \sin[2\ pi\ f2(2D/c)], \quad \text{[Equation 9]}$$

where f2 is the center frequency of the pulse, D is the displacement amplitude of the oscillating scatterer, and c is the speed of sound in the medium. The variation is at a frequency of PRF/2, as can be seen in FIG. 3B Reference is now made to FIG. 4, which is a schematic illustration of a HIFU transducer and an acoustic probe both placed against skin of a subject, according to some applications of the present invention. Apparatus is provided for determining in real-time the location and size of a focal region 46 of a beam of HIFU energy 48 within region 24 of medium 26. It is noted that described hereinbelow is a method for locating focal region 46 in real-time without the use of magnetic resonance imaging (MRI). (MRI is a more expensive way of achieving a corresponding result.) An ultrasound transducer 50 generates first acoustic field 22 (such as is shown in FIG. 1) into region 24 of medium 26 of a subject, by emitting HIFU energy 48 into region 24 at first frequency f1. HIFU energy 48 generates oscillatory motion of scatterers within medium 26, e.g., tissue 52 of a subject, the scatterers oscillating at first frequency f1. Typically, ultrasound transducer 50 emits HIFU energy 48 at a frequency of at least 0.1 MHz and/or less than 5 MHz. An acoustic probe 54 emits pulse-echo ultrasound energy 56 into medium 26 at an imaging frequency, e.g., at a frequency of at least 1 MHz and/or less than 50 MHz. Ultrasonic A-lines, such as A-line 55, comprising acoustic pulses, such as first acoustic pulse 32 and second acoustic pulse 34 as described hereinabove, are transmitted into region 24 of medium 26 by either acoustic probe 54, ultrasound transducer 50, or a second ultrasound transducer 58 (configuration not shown). Each acoustic pulse has a center frequency f2 that is higher, e.g., at least 5 and/or less than 50 times higher, than first frequency f1 of HIFU energy 48, and a time interval between the pulses is n+0.5 times the period T1 of HIFU energy 48, n being a positive integer as described hereinabove. (It is noted that all options that are described herein with respect to the second acoustic field being transmitted by either ultrasound transducer 50, acoustic probe 54, or second ultrasound transducer 58 are interchangeable.) The acoustic pulses are synchronized with HIFU energy, as described hereinabove, and scatter off oscillating scatterers, such as scatterer 28, in medium 26, resulting in respective echoes that are received by acoustic probe 54. (It is noted that all options and features of the invention as described hereinabove with respect to the pulses not being synchronized with first acoustic field 22 can be applied here as well.)

Computer processor 29 (*a*) generates a real-time sonogram 60 of medium 26 from reflections of pulse-echo ultrasound energy 56, (b) extracts a time shift dT between the received echoes, (c) based on the extracted time shift dT, calculates a displacement amplitude D of scatterer 28, and (d) generates a map 62 of displacement amplitudes on a portion 64 of sonogram 60 that corresponds to region 24. As described hereinabove, velocity amplitudes and intensity may be mapped as well.

Map 62 shows where the displacement amplitude or velocity amplitude of oscillating scatterers in first acoustic field 22 is highest, thereby showing where the intensity of first acoustic field 22 is highest, i.e., where focal region 46 is. Due to map 62 being overlaid on top of sonogram 60 of medium 26, focal region 46 can be seen with respect to region 24 in medium 26. Focal region 46 can then be relocated, for example by using a targeting unit as described hereinbelow, as appropriate so as to focus HIFU energy 48 on target location 66 within region 24 of medium 26.

For some applications, medium 26 is tissue 52 of a subject 68 (FIG. 4). Ultrasound transducer 50 causes a therapeutic effect in tissue 52 by emitting HIFU energy 48 into tissue 52. For some applications, the therapeutic affect is caused by HIFU energy 48 heating tissue 52. Other, non-thermal therapeutic effects can be caused by HIFU energy 48 as well, such as, for example, cavitation, tissue liquefaction, cell necrosis, and cell apoptosis.

For some applications, computer processor 29 also monitors a change in a mechanical property of tissue 52 by monitoring a time variation of displacement amplitude D over a time period of at least 1 and/or less than 120 seconds. When the mechanical property of tissue 52 being monitored reaches a threshold value, computer processor 29 terminates transmission of HIFU energy 48. For example, due to exposure to HIFU energy 48 the mechanical impedance of tissue 52 changes. As the mechanical impedance of tissue 52 changes, displacement amplitude D of the oscillating scatterer 28, e.g., an inhomogeneity in tissue 52, changes as well. When the mechanical impedance of tissue 52 reaches a threshold value, computer processor 29 terminates transmission of HIFU energy 48 into tissue 52.

In order to facilitate application of HIFU energy 48 to target location 66 in tissue 52, ultrasound transducer 50 may operate in distinct calibration and therapy modes. In each of the modes ultrasound transducer 50 emits HIFU energy 48 with one or more differing respective parameters. Computer processor 29 varies the respective parameters of the calibration and therapeutic modes such that when ultrasound transducer 50 operates in the therapeutic mode, HIFU energy 48 causes a therapeutic effect in tissue 52, whereas when ultrasound transducer 50 operates in the calibration mode, HIFU energy 48 does not cause a therapeutic effect in tissue 52. For example, computer processor 29 may vary one or more parameters from the following set:

- a duration of a pulse of HIFU energy 48, such that when ultrasound transducer 50 operates in the therapeutic mode the duration of the pulse is longer than the duration of the pulse when ultrasound transducer 50 operates in the calibration mode,
- a duty-cycle of HIFU energy 48, such that when ultrasound transducer 50 operates in the therapeutic mode the duty-cycle is higher than the duty-cycle is when ultrasound transducer 50 operates in the calibration mode, and/or
- the power of HIFU energy 48, such that when ultrasound transducer 50 operates in the therapeutic mode the power of HIFU energy 48 is higher than the power of HIFU energy 48 when ultrasound transducer 50 operates in the calibration mode.

Operating ultrasound transducer 50 in calibration mode allows the displacement amplitude, velocity amplitude, and/or intensity of first acoustic field 22 to be mapped and focal region 46 located while not causing any damage to tissue 52. The beam of HIFU energy 48 can then be reoriented in order to relocate focal region 46, and/or the size of focal region 46 can be changed such that target location 66 is inside focal region 46. Thus, focal region 46 can be monitored and guided while ultrasound transducer 50 is in calibration mode, and once focal region 46 is in the right location, ultrasound transducer 50 can be switched to therapeutic mode in order for HIFU energy 48 to cause a therapeutic effect in tissue 52. For some applications, computer processor 29 monitors tissue 52 while ultrasound transducer 50 operates in therapeutic mode in order to monitor how treatment is progressing. If appropriate, computer processor 29 may vary the abovementioned parameters of ultrasound transducer 50 while ultrasound transducer 50 is operating in therapeutic mode in order to alter an effect on tissue 52 during treatment.

A targeting unit 70 may be used to move focal region 46 of HIFU energy 48. For some applications, targeting unit 70 is configured such that manual movement, e.g., by an operator of ultrasound transducer 50, moves ultrasound transducer 50 with respect to medium 26, thereby moving focal region 46 of HIFU energy 48 within medium 26.

Alternatively or additionally, targeting unit 70 may comprise a first-transducer controller 72 and targeting circuitry 74. Targeting circuitry 74 (a) obtains data corresponding to the location of focal region 46 of HIFU energy 48 on map 62 of displacement amplitudes, velocity amplitudes, or intensities, (b) obtains data corresponding to target location 66 in medium 26, and (c) sends an electric signal to first-transducer controller 72. First-transducer controller 72 receives the electric signal and in response thereto moves focal region 46 of HIFU energy 48 toward target location 66 within medium 26. For example, first-transducer controller 72 may move focal region 46 and/or change a size of focal region 46 by (a) applying phased-array control to HIFU energy 48, or (b) by moving ultrasound transducer 50 with respect to medium 26, e.g., by using a robotic arm 76 and gears to move ultrasound transducer 50 with respect to medium 26. For some applications, targeting circuitry 74 may (a) obtain the data corresponding to the location of focal region 46 and target location 66 directly from computer processor 29, thereby providing closed loop control of the treatment, i.e., computer processor 29 sends data corresponding to the relative positions of focal region 46 and target location 66 to targeting unit 70, via targeting circuitry 74, and targeting unit 70 responds accordingly to bring focal region 46 to target location 66.

Alternatively or additionally, targeting circuitry 74 may (a) obtain real-time data from computer processor 29 corresponding to a size of focal region 46 and (b) send the data to first-transducer controller 72, such that first-transducer controller 72 may change a size of focal region 46 in order to focus or defocus HIFU energy 48. For example, the size of focal region 46 may be (a) decreased in order to increase the intensity of HIFU energy 48 in focal region 46, or (b) increased in order to decrease the intensity of HIFU energy 48 in focal region 46.

Figure 5:
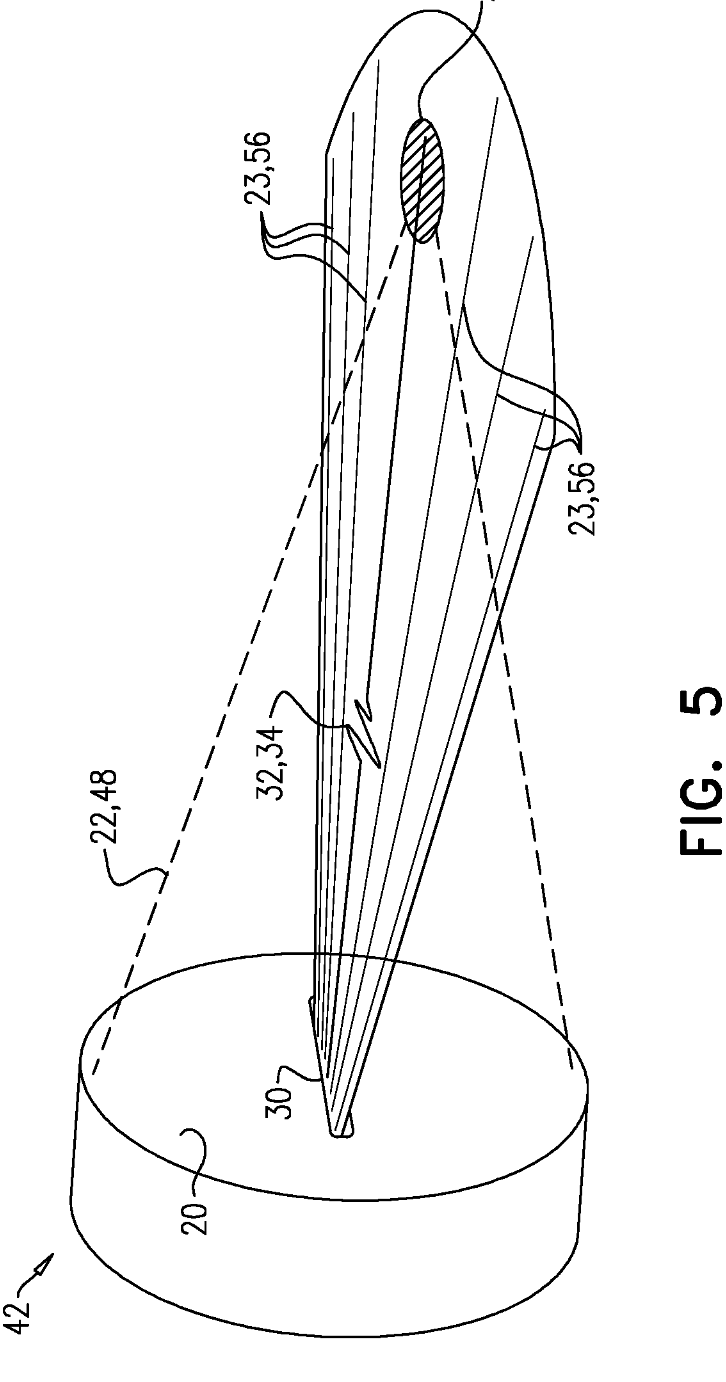
FIG. 5 is a schematic illustration of a HIFU transducer and an acoustic probe disposed on a single unit, according to some applications of the present invention.

Reference is now made to FIG. 5, which is a schematic illustration of a HIFU transducer and an acoustic probe disposed on a single unit, according to some applications of the present invention. First acoustic transducer 20 may be shaped to have a central hole, and second acoustic transducer 30 positioned behind or inside first transducer 20, such that first acoustic field 22 and the diagnostic acoustic pulses are aligned, i.e., such that the axis of first acoustic field 22 and the direction of propagation of the diagnostic acoustic pulses are aligned. For example, Sonic-Concepts H184-002, as well as other models, have a central hole of diameter of about 40 mm.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 29. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 29) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of applications of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 29) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 29 is typically a hardware device programmed with computer program instructions to produce a special purpose computer. For example, when programmed to perform the methods described herein, the computer processor typically acts as a special purpose computer processor. Typically, the operations described herein that are performed by computer processors transform the physical state of a memory, which is a real physical article, to have a different magnetic polarity, electrical charge, or the like depending on the technology of the memory that is used.

Techniques and apparatus described herein may be combined with techniques and apparatus described in U.S. 62/363,295 to Ben-Ezra, filed Jul. 17, 2016, entitled, "Doppler guided ultrasound therapy," and PCT/IL2017/050799 to Ben-Ezra, filed Jul. 13, 2017, which published as WO 2018/015944 to Ben-Ezra, entitled, "Doppler guided ultrasound therapy," which are both incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a focal region of high intensity focused ultrasound (HIFU) energy, the apparatus comprising:

a first ultrasound transducer configured to transmit a first acoustic field by emitting the HIFU energy into a medium at a first frequency, a propagation of the first acoustic field generating oscillatory motion at the first frequency of scatterers disposed in the medium, (i) each scatterer oscillating around a respective equilibrium position, and (ii) the oscillatory motion of the scatterers being an acoustic particle-velocity of the first acoustic field;

an acoustic probe, wherein the acoustic probe is configured to emit pulse-echo ultrasound energy into the medium at an imaging frequency, and wherein an acoustic element selected from a group consisting of the first ultrasound transducer, a second ultrasound transducer, and the acoustic probe is configured to (i) transmit a plurality of pairs of first and second acoustic pulses into the focal region in a plurality of respective directions while the HIFU energy is being emitted, each pulse having a center frequency that is higher than the first frequency, a time interval between the first and second pulses of each respective pair being n+0.5 times a period of the first acoustic field, n being a positive integer, and (ii) receive respective pairs of echoes of each pair of pulses scattering off a respective oscillating scatterer in the focal region, the plurality of pairs of first and second pulses being synchronized with the first acoustic field such that, for each pair, the first pulse scatters off the respective oscillating scatterer when the respective oscillating scatterer is at a first displacement extremum with respect to the equilibrium position, and the second pulse scatters off the respective oscillating scatterer when the respective oscillating scatterer is at a second displacement extremum that is opposite the first displacement extremum with respect to the equilibrium position; and a computer processor configured to (a) generate a real-time sonogram of the medium based on reflections of the pulse-echo ultrasound energy that is transmitted by the acoustic probe, (b) extract respective time shifts, each respective time shift being between the received echoes of a respective pair of echoes that are due to motion of the respective oscillating scatterer, (c) based on the extracted respective time shifts, calculate displacement amplitudes of the respective oscillating scatterers, and (d) generate a map of the displacement amplitudes on a portion of the sonogram corresponding to the focal region.

2. The apparatus according to claim 1, wherein the acoustic element comprises the acoustic probe.

3. The apparatus according to claim 1, wherein the acoustic element comprises the first ultrasound transducer.

4. The apparatus according to claim 1, wherein the first frequency is 0.1-5 MHz.

5. The apparatus according to claim 1, wherein the center frequency of each pulse is 5 to 50 times higher than the first frequency.

6. The apparatus according to claim 1, further comprising a single housing to which the first ultrasound transducer and the acoustic element are coupled, wherein the housing aligns the first acoustic field and the acoustic pulses to be parallel or anti-parallel.

7. The apparatus according to claim 1, wherein the computer processor is further configured to (a) based on the displacement amplitudes, calculate velocity amplitudes of the first acoustic field in the focal region, and (b) generate a map of the velocity amplitudes on a portion of the sonogram corresponding to the focal region.

8. The apparatus according to claim 7, wherein the computer processor is further configured to (a) based on the velocity amplitudes, calculate intensities of the first acoustic field in the focal region, and (b) generate a map of the intensities of the first acoustic field on a portion of the sonogram corresponding to the focal region.

9. The apparatus according to claim 1, wherein the medium is tissue of a body of a subject and wherein the first ultrasound transducer is configured to cause a therapeutic effect in the tissue by emitting the HIFU energy into the tissue, and wherein the computer processor is further configured to:

(a) based on the displacement amplitudes, calculate velocity amplitudes of the first acoustic field in the focal region;

(b) monitor a change in a mechanical property of the tissue by monitoring a time variation of the displacement amplitudes; and (c) in response to the monitoring, terminate the first acoustic field when the mechanical property of the tissue reaches a threshold value.

10. The apparatus according to claim 9, wherein the mechanical property of the tissue is mechanical impedance of the tissue, and wherein the computer processor is configured to (a) monitor a change in the mechanical impedance of the tissue by monitoring a time variation of the displacement amplitudes, and (b) in response to the monitoring, terminate the first acoustic field when the mechanical impedance of the tissue reaches a threshold value.

11. The apparatus according to claim 9, wherein the computer processor is configured to monitor the change in the mechanical property of the tissue over a time period that is 1-120 seconds long.

12. The apparatus according to claim 1, wherein:

the medium is tissue of a body of a subject and wherein the first ultrasound transducer is configured to cause a therapeutic effect in the tissue by emitting the HIFU energy into the tissue, the first ultrasound transducer is configured to operate in distinct calibration and therapy modes to facilitate application of therapeutic HIFU energy to a target location, in each of the modes emitting the HIFU energy with one or more differing respective parameters, and the computer processor is configured to vary the one or more respective parameters such that when the first ultrasound transducer operates in the therapeutic mode the HIFU energy causes the therapeutic effect in the tissue whereas when the first ultrasound transducer is operating in the calibration mode the HIFU energy does not cause the therapeutic effect in the tissue.

13. The apparatus according to claim 12, wherein the computer processor is configured to vary a duration of a HIFU-pulse of the HIFU energy, such that when the first ultrasound transducer operates in the therapeutic mode the duration of the HIFU-pulse is longer than the duration of the HIFU-pulse is when the first ultrasound transducer operates in the calibration mode.

14. The apparatus according to claim 12, wherein the computer processor is configured to vary a duty-cycle of the HIFU energy, such that when the first ultrasound transducer operates in the therapeutic mode the duty-cycle is higher than the duty-cycle is when the first ultrasound transducer operates in the calibration mode.

15. The apparatus according to claim 12, wherein the computer processor is configured to vary a power of the HIFU energy, such that when the first ultrasound transducer operates in the therapeutic mode the power of the HIFU energy is higher than the power of the HIFU energy is when the first ultrasound transducer operates in the calibration mode.

16. The apparatus according to claim 12, wherein the computer processor is configured to monitor the tissue when the first ultrasound transducer operates in the therapeutic mode and to vary the parameters of the therapeutic mode according to the monitoring in order to alter an effect on the tissue.

17. The apparatus according to claim 12, wherein the apparatus comprises a targeting unit configured to move the focal region of the HIFU energy when the first ultrasound transducer operates in the calibration mode.

18. The apparatus according to claim 17, wherein the targeting unit is configured such that manual movement of the targeting unit moves the focal region of the HIFU energy within the medium by moving the first ultrasound transducer with respect to the medium.

19. The apparatus according to claim 17, wherein:

(A) the computer processor is further configured to (i) based on the displacement amplitudes, calculate velocity amplitudes of the first acoustic field in the focal region, (ii) generate a map of the velocity amplitudes on a portion of the sonogram corresponding to the focal region, (iii) based on the velocity amplitudes, calculate intensities of the first acoustic field in the focal region, and (iv) generate a map of the intensities of the first acoustic field on a portion of the sonogram corresponding to the focal region, and (B) the targeting unit comprises (i) a first-transducer controller and (ii) targeting circuitry configured to (a) obtain data corresponding to the focal region of the HIFU energy on a map selected from the group consisting of: the map of displacement amplitudes, the map of velocity amplitudes, and the map of intensities, (b) obtain data corresponding to a target location in the medium, and (c) send an electric signal to the first-transducer controller, wherein the first-transducer controller is configured to receive the electric signal and in response thereto move the focal region of the HIFU energy toward the target location within the medium.

20. The apparatus according to claim 19, wherein the first-transducer controller is configured to (a) move the focal region of the HIFU energy with respect to the first ultrasound transducer, and (b) change a size of the focal region of the HIFU energy by applying phased-array control to the HIFU energy emitted by the first ultrasound transducer.

* * * * *